(12) United States Patent
Hattori

(10) Patent No.: US 6,978,653 B2
(45) Date of Patent: Dec. 27, 2005

(54) ABNORMALITY DETECTION SYSTEM OF OXYGEN SENSOR AND ABNORMALITY DETECTION METHOD THEREOF

(75) Inventor: Kazutaka Hattori, Okazaki (JP)

(73) Assignee: Toyota Jidosha Kabushiki Kaisha, Toyota (JP)

(*) Notice: Subject to any disclaimer, the term of this patent is extended or adjusted under 35 U.S.C. 154(b) by 147 days.

(21) Appl. No.: 10/790,805

(22) Filed: Mar. 3, 2004

(65) Prior Publication Data

US 2004/0187554 A1 Sep. 30, 2004

(30) Foreign Application Priority Data

Mar. 24, 2003 (JP) .............................. 2003-079892

(51) Int. Cl.[7] .............................................. G01M 1/00
(52) U.S. Cl. ...................................................... 73/1.06
(58) Field of Search ............................. 73/1.06, 118.1, 73/23.32

(56) References Cited

U.S. PATENT DOCUMENTS 6,164,125 A * 12/2000 Kawase et al. ............ 73/118.1

FOREIGN PATENT DOCUMENTS

| JP | A 8-327586 | 12/1996 |
|----|------------|---------|
| JP | A 8-338823 | 12/1996 |
| JP | A 9-274006 | 10/1997 |
| JP | A 2000-46780 | 2/2000 |
| JP | A 2001-20804 | 1/2001 |

* cited by examiner

*Primary Examiner*—Robert Raevis

(74) *Attorney, Agent, or Firm*—Oliff & Berridge PLC

(57) ABSTRACT

In an abnormality detection system that detects abnormality in an oxygen sensor including a detection element for outputting a current value corresponding to an oxygen concentration upon receipt of a voltage application, a negative value is applied to the oxygen sensor so as to obtain an impedance of the detection element. Then a difference between the obtained impedance of the oxygen sensor upon application of the negative voltage and the impedance of the oxygen sensor upon application of a positive voltage prior to the negative voltage application is calculated. It is determined whether there is abnormality in the oxygen sensor based on the calculated difference.

15 Claims, 4 Drawing Sheets

ABNORMALITY DETECTION SYSTEM OF OXYGEN SENSOR AND ABNORMALITY DETECTION METHOD THEREOF

INCORPORATION BY REFERENCE

The disclosure of Japanese Patent Application No.2003-79892 filed on Mar. 24, 2003, including the specification, drawings and abstract are incorporated herein by reference in its entirety.

BACKGROUND OF THE INVENTION

1. Field of Invention

The invention relates to an abnormality detection system of an oxygen sensor used as an air fuel ratio sensor for a vehicle, and an abnormality detection method of the oxygen sensor.

2. Description of Related Art

It has been well known to set an air fuel ratio of air fuel mixture within a combustion chamber of an internal combustion engine at a desired value based on a concentration of oxygen contained in exhaust gas discharged from the combustion chamber, which is detected by an oxygen sensor. The oxygen sensor of critical current type, for example, has been conventionally used as the oxygen sensor of the above-described type. The oxygen sensor of critical current type includes a detection element formed of a solid electrolyte having inner and outer surfaces provided with electrodes, respectively. The inner surface of the detection element admits air to be introduced, and the outer surface of the detection element admits exhaust gas discharged from a combustion chamber. When voltage is applied between the electrodes of the detection element, it outputs a current (critical current) value corresponding to the oxygen concentration of the exhaust gas.

When the detection element of the oxygen sensor is deteriorated, or cracked owing to a certain cause, air that exists on the inner surface of the detection element is mixed with the exhaust gas that exists on the outer surface of the detection element. This may prevent the oxygen sensor from accurately detecting the oxygen concentration of the exhaust gas or the like. The process for applying negative voltage to the oxygen sensor has been generally used so as to detect the aforementioned abnormality in the oxygen sensor. In response to the application of the negative voltage, the oxygen sensor outputs a current value, based on which it is determined whether there is abnormality such as the crack. The aforementioned process is disclosed in JP-A-8-327586, for example.

In the case where the negative voltage is applied to the oxygen sensor in the generally employed process, a certain length of time (about several seconds) will be taken until the current value output from the oxygen sensor is stabilized. Accordingly, it is difficult for the aforementioned process to detect the abnormality in the oxygen sensor rapidly with good response. Execution of the abnormality detection process (for several seconds) as aforementioned may hinder the air fuel ratio control executed by the oxygen sensor.

SUMMARY OF THE INVENTION

It is an object of the invention to provide an abnormality detection system and an abnormality detection method of an oxygen sensor which may allow detection of the abnormality in the oxygen sensor rapidly with good response.

According to a first aspect of the invention, an abnormality detection system that detects abnormality in an oxygen sensor which outputs a current value corresponding to an oxygen concentration upon receipt of a voltage application is provided with a voltage application unit that applies a voltage to the oxygen sensor and switches polarity of the applied voltage between a positive voltage and a negative voltage, and a controller that obtains an impedance of the oxygen sensor, and determines whether there is abnormality in the oxygen sensor based on a difference between the impedance of the oxygen sensor obtained when the positive voltage is applied to the oxygen sensor by the voltage application unit and the impedance of the oxygen sensor obtained when the negative voltage is applied to the oxygen sensor by the voltage application unit.

According to the first aspect, it is determined whether there is abnormality in the oxygen sensor based on a difference between an impedance of the oxygen sensor upon application of the negative voltage and an impedance of the oxygen sensor upon application of the positive voltage prior to the application of the negative voltage. This may stabilize the impedance of the oxygen sensor (detection element) immediately after the application of the negative voltage. As a result, the abnormality detection of the oxygen sensor can be executed rapidly with good response.

It is preferable to apply the negative voltage to the oxygen sensor when a predetermined condition for detecting abnormality is established. The abnormality detection of the oxygen sensor is executed only when the predetermined condition is established.

It is further preferable to detect the impedance of the oxygen sensor with volts alternating current (VAC) at high frequency. This may allow accurate detection of the impedance of the oxygen sensor with no need of considering the interface resistance of the electrodes in the oxygen sensor (detection element) which tends to vary with aged deterioration and the like. The abnormality in the oxygen sensor, thus, can be accurately detected.

According to a second aspect of the invention, in an abnormality detection method of detecting abnormality in an oxygen sensor for outputting a current value corresponding to an oxygen concentration upon receipt of a voltage application, an impedance of the oxygen sensor is obtained by applying a negative voltage to the oxygen sensor, and it is determined whether there is abnormality in the oxygen sensor based on a difference between the impedance of the oxygen sensor obtained when the negative voltage is applied to the oxygen sensor and the impedance oxygen sensor obtained when a positive voltage is applied to the oxygen sensor prior to the application of the negative voltage.

According to a third aspect of the invention, an abnormality detection system that detects abnormality in an oxygen sensor which outputs a current value corresponding to an oxygen concentration upon receipt of a voltage application is provided with impedance obtaining means for obtaining an impedance of the oxygen sensor, voltage application means for applying a voltage to the oxygen sensor and switches polarity of the applied voltage between a positive voltage and a negative voltage, and determination means for determining whether there is abnormality in the oxygen sensor based on a difference between the impedance of the oxygen sensor obtained when the positive voltage is applied to the oxygen sensor by the voltage application means and the impedance of the oxygen sensor obtained when the negative voltage is applied to the oxygen sensor by the voltage application means.

BRIEF DESCRIPTION OF THE DRAWINGS

The foregoing and further objects, features and advantages of the invention will become apparent from the following description of preferred embodiments with reference to the accompanying drawings, wherein like numerals are used to represent like elements and wherein.

DETAILED DESCRIPTION OF THE PREFERRED EMBODIMENTS

Figure 1:
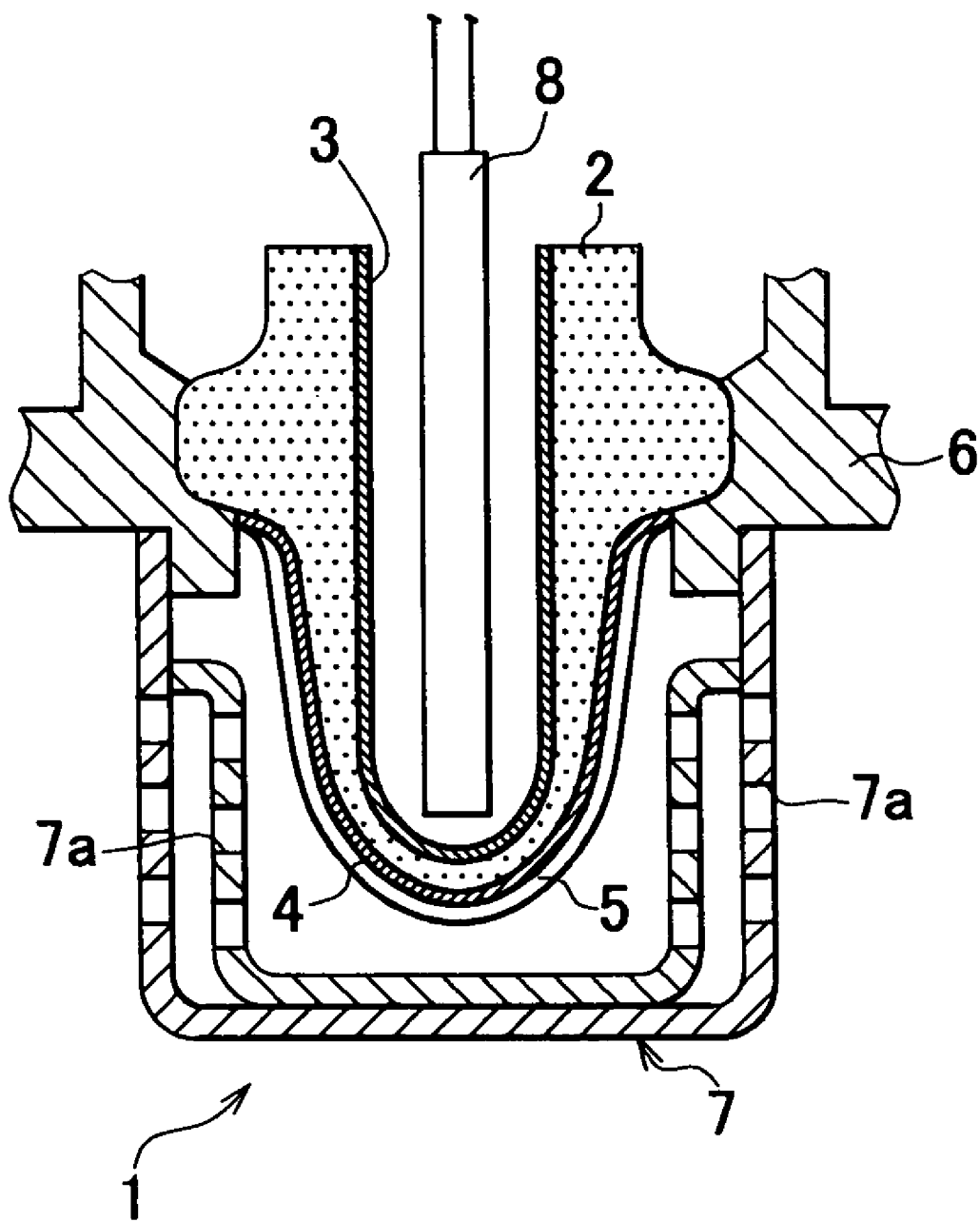
FIG. 1 is a sectional view of an oxygen sensor subjected to detection performed by an abnormality detection system according to the invention.

An abnormality detection system and an abnormality detection method of an oxygen sensor according to an embodiment of the invention will be described referring to the drawings.

Figure 2:
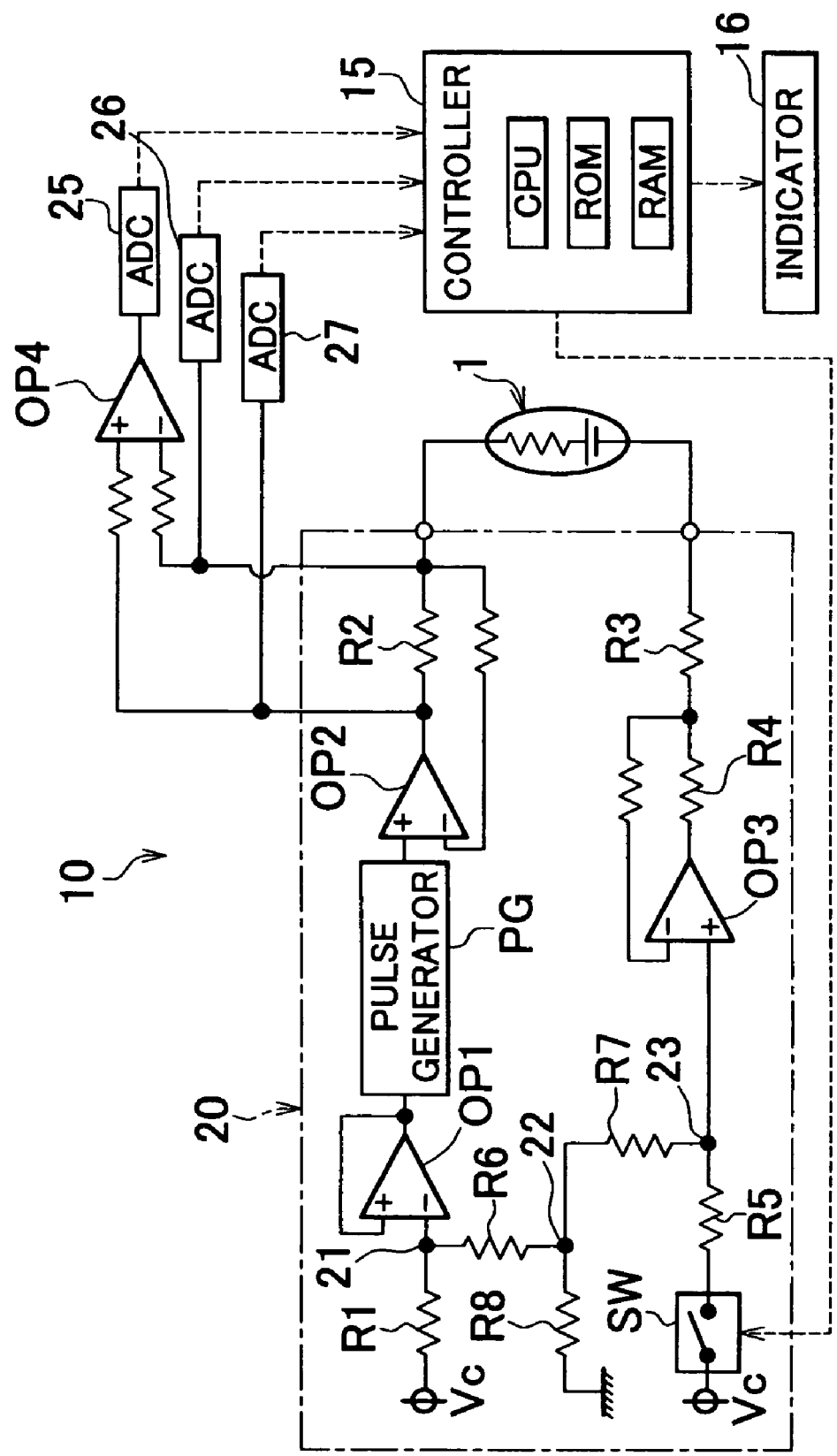
FIG. 2 is a block diagram that shows the abnormality detection system of the oxygen sensor according to the invention.

FIG. 1 is an enlarged sectional view showing an oxygen sensor subjected to abnormality detection performed by the abnormality detection system of the embodiment. FIG. 2 is a block diagram showing the abnormality detection system of the oxygen sensor. An oxygen sensor 1 shown in FIG. 1 is used as an air fuel ratio sensor in an internal combustion engine for a vehicle. The oxygen sensor 1 includes a detection element 2 formed of a solid electrode, for example, zirconia, titania and the like. The detection element 2 is formed into a bottomed cylindrical shape, and has an inner surface provided with a platinum electrode 3 and an outer surface provided with a platinum electrode 4. A diffused resistor layer (protective coating) 5 is laminated on the platinum electrode 4 on the outer surface of the detection element 2.

The detection element 2 is supported by a housing 6 to which a protection cover 7 for covering the detection element 2 is fixed. The protection cover 7 has a plurality of holes 7a as shown in FIG. 1. The oxygen sensor 1 is placed such that the protection cover 7 is fit in an exhaust pipe (exhaust manifold). Accordingly the exhaust gas flowing through an exhaust system is admitted in the space between the platinum electrode 4 provided on the outer surface of the detection element 2 and the protection cover 7. Meanwhile a heater 8 is placed in the inner space (in contact with the platinum electrode 3) of the detection element 2 so as to admit air to be introduced therein. The heater 8 is connected to a heater current control circuit (not shown) and a power supply (not shown). The current applied to the heater 8 is controlled to adjust the temperature of the detection element 2 such that a degree of activation of the detection element 2 is changed.

Referring to FIG. 2, the oxygen sensor 1 is connected to a voltage application portion 20 which is controlled by a controller 15. The controller 15 and the voltage application portion 20 constitute an abnormality detection unit 10 of the oxygen sensor 1. The controller 15 includes CPU, ROM, RAM and the like, and controls the voltage application portion 20 for applying voltage to the oxygen sensor 1 so as to obtain an air fuel ratio of the exhaust gas flowing through the exhaust system based on an output value of the oxygen sensor (detection element 2).

The voltage application portion 20 includes a constant voltage source Vc that is connected to a pulse generator PG via a resistance R1 and an operational amplifier or Op-Amp OP1. The pulse generator PG is connected to the platinum electrode 3 on the inner surface (atmospheric side) of the oxygen sensor 1 via an operational amplifier or Op-Amp OP2 and a resistance R2. The pulse generator PG serves to superpose a pulse voltage (±0.2 V) at a predetermined frequency (for example, in the range between 1 and 10 KHz) on a voltage signal supplied from the constant voltage source Vc. Meanwhile, an operational amplifier or Op-Amp OP3 is connected to the platinum electrode 4 on the outer surface (exhaust side) of the oxygen sensor 1 via resistances R3 and R4. A non-inverting input terminal of the Op-Amp OP3 is connected to the constant voltage source Vc via a resistance R5 and a switching element SW that is turned ON/OFF by the controller 15.

A terminal 21 interposed between the resistance R1 and the Op-Amp OP1 is connected to one end of a resistance R6. The other end of the resistance R6 is connected to a terminal 22. A terminal 23 interposed between the resistance R5 and the Op-Amp O3 is connected to one end of a resistance R7. The other end of the resistance R7 is connected to the terminal 22. The terminal 22 is connected to a resistance R8 having one end grounded. Assuming that the potential in the terminal 21 is 3.3 V, for example, each value of the resistances R1 to R8 is set such that the potential in the terminal 22 becomes 2.9 V upon turning the switching element SW OFF, and the potential in the terminal 23 becomes 3.7 V upon turning the switching element SW ON.

When the air fuel ratio within the internal combustion engine is detected using the oxygen sensor 1, the controller 15 turns the switching element SW OFF and the voltage application portion 20 applies positive voltage (+0.4 V) to the oxygen sensor 1. Application of the positive voltage to the portion between the electrodes 3 and 4 in the oxygen sensor 1 allows the detection element 2 to output a current (critical current) value corresponding to the oxygen concentration within the exhaust gas. The output current value of the detection element 2 is sent to the controller 15 via an AID converter 25 connected to both ends of the resistance R2 through the Op-Amp OP4 such that the air fuel ratio within the internal combustion engine is calculated.

A/D converters 26, 27 are connected to both ends of the resistance R2. Based on output values of the A/D converters 26, 27, the controller 15 obtains the impedance of the detection element 2 upon application of the voltage (positive high frequency volts alternating current or positive high frequency VAC) to the oxygen sensor 1 by the voltage application portion 20. Based on the obtained impedance of the detection element 2, the controller 15 serves to determine whether there is abnormality in the oxygen sensor 1. The controller 15 further obtains temperature of the detection element 2 based on the impedance of the detection element 2, and controls the heater current control circuit (not shown) for the heater 8 such that the obtained temperature of the detection element 2 becomes the desired value.

The procedure for determining the abnormality in the oxygen sensor 1 will be described referring to FIG. 3.

Figure 3:
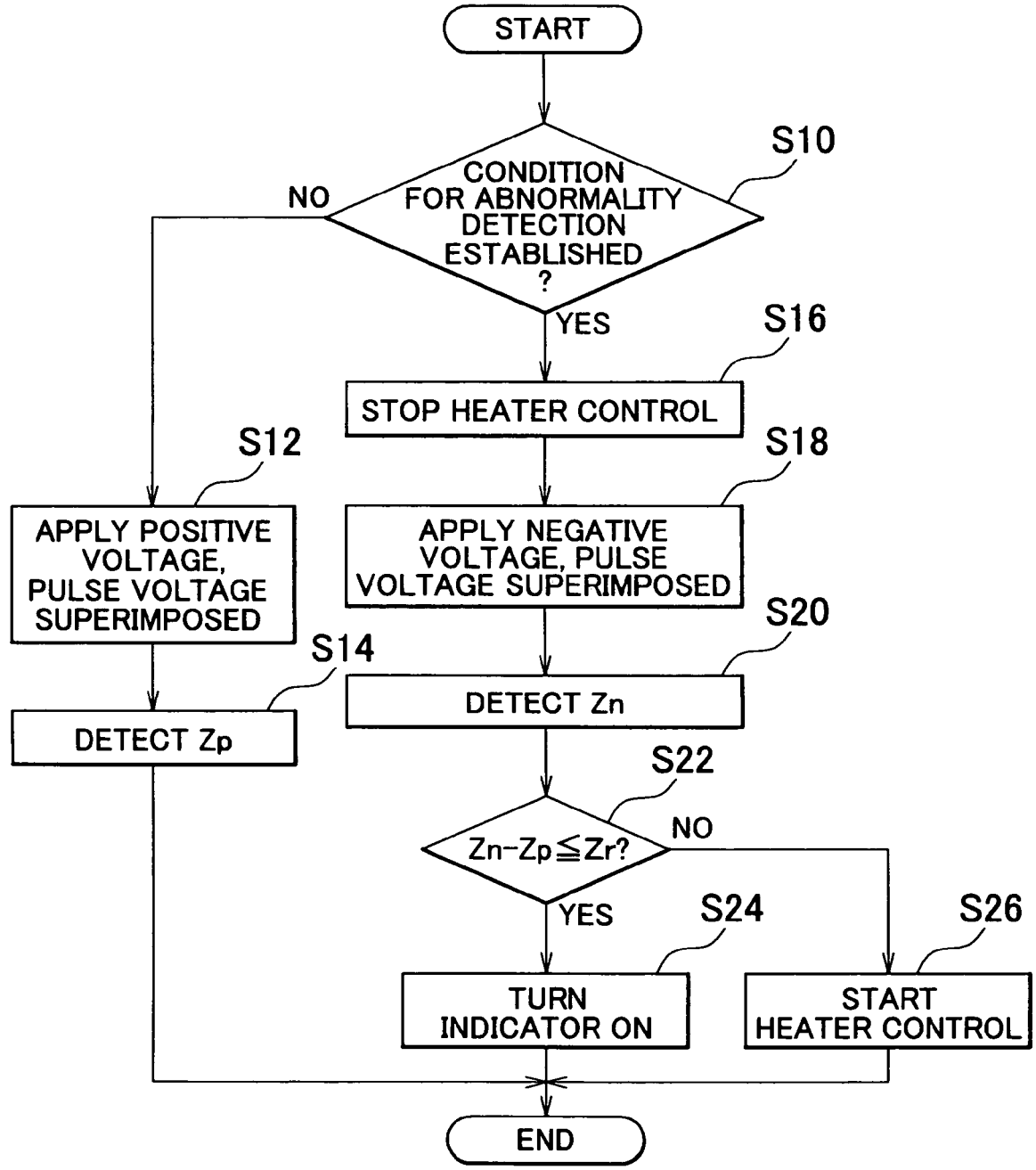
FIG. 3 is a flowchart representing a control routine for detecting abnormality in the oxygen sensor executed by the abnormality detection system as shown in FIG. 2.

The control routine for detecting the abnormality in the oxygen sensor 1 as shown by the flowchart in FIG. 3 is executed by the controller 15 that constitutes the abnormality detection unit 10 for the oxygen sensor 1 at a predetermined time interval of about 65 msec., for example. The controller 15 determines establishment of a condition for detecting the abnormality in the oxygen sensor 1 at every passage of the predetermined time period in step S10.

There may be the case where during an engine operation, after passage of a predetermined time period from stop of the fuel supply (fuel injection) to the engine, further fuel supply (fuel injection) is interrupted. In the aforementioned case, the oxygen concentration within the exhaust gas is increased, and the difference of the oxygen concentration between the exhaust gas and air may be reduced. It is, therefore, difficult to accurately distinguish the reduced difference owing to the aforementioned cause from the reduced difference which is caused by the crack and the like. The abnormality detection unit 10 is controlled to detect the abnormality in the oxygen sensor only when it is determined that the predetermined condition for detecting the abnormality is established in step S10, for example, when a predetermined time period passes from stop of the fuel injection and no further fuel injection is performed.

When it is determined that the condition for detecting the abnormality has not been established in step S10, the controller 15 turns the switching element SW of the voltage application portion 20 OFF and operates the pulse generator PG in step S12. As a result, the positive high frequency VAC (between 0.6 and 0.2 V) is applied by the voltage application portion 20 to the portion between the electrodes 3 and 4 in the oxygen sensor 1. In step S14, based on signals from the A/D converters 26, 27, the controller 15 detects an impedance Zp of the detection element 2 obtained when the positive high frequency VAC is applied to the oxygen sensor 1 in step S12. The obtained impedance Zp of the detection element 2 is then stored in a predetermined storage area in the controller 15. Subsequent to the process in step S14, the controller 15 stands until the timing for executing the control routine next, that is, until the passage of time-for about 65 msec.

When it is determined that the condition for detecting the abnormality has been established in step S10, the controller stops the control of the heater 8 which is to be executed based on the impedance of the detection element 2 in step S16. Then in step S18, the controller 15 turns the switching element SW of the voltage application portion 20 ON, and activates the pulse generator PG. This may allow the voltage application portion 20 to apply negative high frequency VAC (between −0.6 V and −0.2 V) to the portion between the electrodes 3 and 4 of the oxygen sensor 1. Then in step S20, the controller 15 detects an impedance Zn of the detection element 2 upon application of the negative high frequency VAC to the oxygen sensor 1 in step S18.

Figure 4:
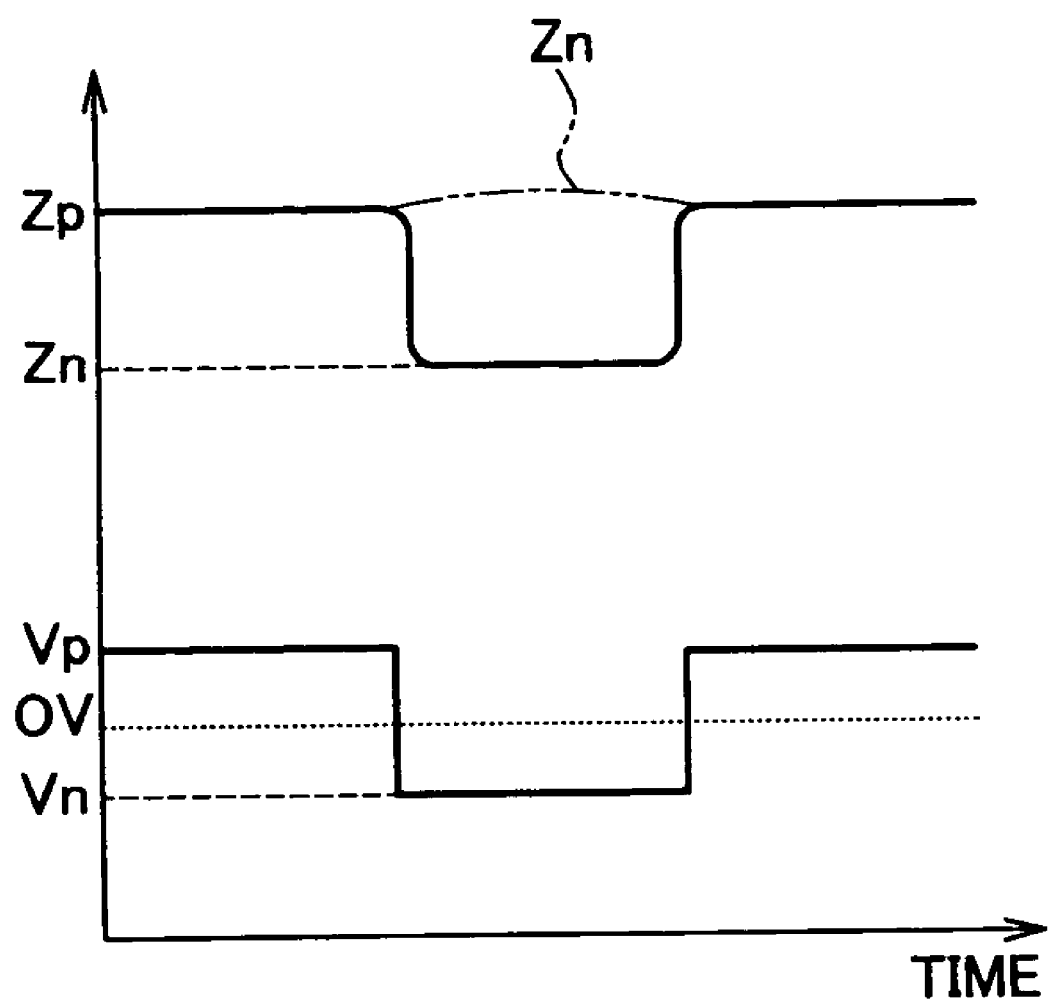
FIG. 4 is a timing chart that indicates a change in the impedance of the detection element upon reverse of the polarity of the voltage to be applied to the oxygen sensor.

In the case where the positive voltage is applied to the oxygen sensor 1, the impedance of the detection element 2 takes the value corresponding to the oxygen concentration of the exhaust gas in contact with the electrode 4 on the outer surface of the element. In the case where the negative voltage is applied to the oxygen sensor 1, the impedance of the detection element 2 takes the value corresponding to the oxygen concentration of atmosphere in contact with the electrode 3 on the inner surface of the element. If the oxygen sensor 1 (detection element 2) is in the normal state, the impedance of the detection element 2 is reduced from Zp to Zn to a predetermined degree as shown by a solid line in FIG. 4 upon inversion of the polarity of the voltage applied to the oxygen sensor 1 from positive (Vp) to negative (Vn). If there is a crack in the detection element 2, the difference between the impedance of the detection element 2 before inversion of the polarity of the applied voltage and after inversion of the polarity of the applied voltage is substantially smaller than the one in the case where the oxygen sensor 1 is in the normal state as shown by the chain double dashed line of FIG. 4.

Accordingly the abnormality detection unit 10 is used for determining whether there is abnormality in the oxygen sensor 1 (detecting element 2) based on the change (difference: Zn−Zp) in the impedance of the detection element 2 between before and after inversion of the polarity in the voltage applied to the oxygen sensor 1. That is, the controller 15 obtains the impedance Zn of the detection element 2 upon application of the negative high frequency VAC to the oxygen sensor 1 in step S20. Then the difference between the obtained impedance Zn and the impedance Zp obtained in step S14 upon application of the positive voltage to the oxygen sensor 1, that is, Zn−Zp is obtained. Then in step S22, it is determined whether the obtained difference, that is, Zn−Zp is equal to or less than a predetermined threshold value Zr.

When it is determined that the difference of the impedance of the detection element 2 between before and after the inversion of the polarity of the voltage applied to the oxygen sensor 1, that is, Zn−Zp, is equal to or less than the threshold value Zr, it is determined that the abnormality such as crack may occur in the element of the oxygen sensor 1. The process then proceeds to step S24 where an indicator 16 (see FIG. 2) placed at a predetermined position of the vehicle is illuminated. Subsequently the controller 15 stands until the timing for executing the next control routine (passage of 65 msec.).

When it is determined that the difference of the impedance of the detection element 2, that is, Zn−Zp, exceeds the threshold value in step S22, it is determined that the oxygen sensor 1 is in the normal state. The process then proceeds to step S26 to resume the control of the heater 8 based on the impedance of the detection element 2, which has been stopped in step S16. After executing step S14, the controller 15 stands until the timing for executing the next control routine (passage of 65 msec.).

Execution of the aforementioned control routine allows the impedance of the detection element 2 to be stabilized immediately after application of the negative voltage. Therefore, the abnormality detection unit 10 makes it possible to execute the detection of abnormality in the oxygen sensor 1 rapidly with good response. The abnormality detection unit 10 is capable of detecting the impedance of the detection element 2 accurately with the high frequency VAC. This makes it possible to detect abnormality in the oxygen sensor 1 accurately with no need of considering the interface resistance of the electrodes of the oxygen sensor 1 (detection element 2) that varies with the aged deterioration. In the example of the control routine shown in FIG. 3, execution of the control of the heater 8 based on the impedance of the detection element 2 is stopped in step S16. However, it is to be understood that the control routine is not limited to the one as described above. In the example as shown in FIG. 3, the heater 8 may be controlled in steps from S16 to S26 by correcting the impedance of the detection element 2.

The above embodiment makes it possible to rapidly execute detection of abnormality in the oxygen sensor with good response.

What is claimed is:

1. An abnormality detection system that detects abnormality in an oxygen sensor which outputs a current value corresponding to an oxygen concentration upon receipt of a voltage application, the abnormality detection system comprising:

a voltage application unit that applies a voltage to the oxygen sensor and switches polarity of the applied voltage between a positive voltage and a negative voltage; and a controller that obtains an impedance of the oxygen sensor, and determines whether there is abnormality in the oxygen sensor based on a difference between the impedance of the oxygen sensor obtained when the positive voltage is applied to the oxygen sensor by the voltage application unit and the impedance of the oxygen sensor obtained when the negative voltage is applied to the oxygen sensor by the voltage application unit.

2. The abnormality detection system according to claim 1, wherein the voltage application unit applies the negative voltage to the oxygen sensor when it is determined that a predetermined condition for detecting abnormality is established.

3. The abnormality detection system according to claim 2, wherein the controller obtains the impedance of the oxygen sensor with a high frequency volts alternating current.

4. The abnormality detection system according to claim 2, wherein the predetermined condition is established when a predetermined time period passes from stop of the fuel injection and no further fuel injection is performed.

5. The abnormality detection system according to claim 1, wherein the controller obtains the impedance of the oxygen sensor with a high frequency volts alternating current.

6. The abnormality detection system according to claim 1, wherein it is determined that there is the abnormality in the oxygen sensor when it is determined that the difference of the impedance of the oxygen sensor is equal to or less than a threshold value.

7. The abnormality detection system according to claim 1, wherein the controller determines whether there is abnormality in the oxygen sensor based on a difference between the impedance of the oxygen sensor obtained when the positive voltage is applied to the oxygen sensor and the impedance of the oxygen sensor obtained when the negative voltage is applied to the oxygen sensor after the application of the positive voltage.

8. An abnormality detection method of detecting abnormality in an oxygen sensor for outputting a current value corresponding to an oxygen concentration upon receipt of a voltage application, the method comprising the steps of:

obtaining an impedance of the oxygen sensor by applying a negative voltage to the oxygen sensor; and determining whether there is abnormality in the oxygen sensor based on a difference between the impedance of the oxygen sensor obtained when the negative voltage is applied to the oxygen sensor and the impedance of the oxygen sensor obtained when a positive voltage is applied to the oxygen sensor prior to the application of the negative voltage.

9. The abnormality detection method according to claim 8, wherein the negative voltage is applied to the oxygen sensor when a predetermined condition for detecting abnormality is established.

10. The abnormality detection method according to claim 9, wherein the impedance of the oxygen sensor is obtained with a high frequency volts alternating current.

11. The abnormality detection method according to claim 9, wherein the predetermined condition is established when a predetermined time period passes from stop of the fuel injection and no further fuel injection is performed.

12. The abnormality detection method according to claim 8, wherein the impedance of the oxygen sensor is obtained with a high frequency volts alternating current.

13. The abnormality detection method according to claim 8, wherein it is determined that there is the abnormality in the oxygen sensor when it is determined that the difference of the impedance of the oxygen sensor is equal to or less than a threshold value.

14. The abnormality detection method according to claim 8, wherein it is determined whether there is abnormality in the oxygen sensor based on a difference between the impedance of the oxygen sensor obtained when the positive voltage is applied to the oxygen sensor and the impedance of the oxygen sensor obtained when the negative voltage is applied to the oxygen sensor after the application of the positive voltage.

15. An abnormality detection system that detects abnormality in an oxygen sensor which outputs a current value corresponding to an oxygen concentration upon receipt of a voltage application, the abnormality detection system comprising:

impedance obtaining means for obtaining an impedance of the oxygen sensor;

voltage application means for applying a voltage to the oxygen sensor and switches polarity of the applied voltage between a positive voltage and a negative voltage; and determination means for determining whether there is abnormality in the oxygen sensor based on a difference between the impedance of the oxygen sensor obtained when the positive voltage is applied to the oxygen sensor by the voltage application means and the impedance of the oxygen sensor obtained when the negative voltage is applied to the oxygen sensor by the voltage application means.

* * * * *